United States Patent [19]

Wawro et al.

[11] Patent Number: 5,556,073
[45] Date of Patent: Sep. 17, 1996

[54] LINEAR CONTROL VALVE

[75] Inventors: Thaddeus J. Wawro, Auburn; Alan S. Knieriem, Baldwinsville; Zoran I. Psenicnik, Skaneateles, all of N.Y.; Dale E. Finch, Tampa, Fla.

[73] Assignee: Welch Allyn, Inc., Skaneateles Falls, N.Y.

[21] Appl. No.: 382,286

[22] Filed: Feb. 1, 1995

[51] Int. Cl.$^6$ .................... F16K 31/04; F16K 1/16; A61B 5/02
[52] U.S. Cl. .............. 251/129.11; 128/685; 128/686; 251/249.5; 251/263; 251/303; 606/202
[58] Field of Search ................ 251/11, 129.11, 251/129.12, 129.13, 248, 249.5, 251, 263, 129.3, 303; 128/685, 686; 606/202, 203, 129.2; 604/247

[56] References Cited

U.S. PATENT DOCUMENTS

| | | |
|---|---|---|
| 2,846,181 | 8/1958 | Orelind et al. ............. 251/303 |
| 2,851,959 | 9/1958 | Kangas ..................... 251/129.12 |
| 2,881,786 | 4/1959 | Ogle et al. ................. 251/303 |
| 3,042,357 | 7/1962 | Engholdt ................... 251/129.11 |
| 3,054,426 | 9/1962 | Fritz et al. ................ 251/129.11 |
| 3,095,873 | 7/1963 | Edmunds ................... 128/686 |
| 3,137,475 | 6/1964 | Schoenecker et al. ...... 251/129.11 |
| 3,527,207 | 9/1970 | Gottfried et al. ........... 606/202 |
| 3,613,732 | 10/1971 | Willson et al. ............. 251/11 |
| 3,935,984 | 2/1976 | Lichowsky et al. ......... 128/686 |
| 4,044,913 | 8/1977 | Brunnert .................. 251/303 |
| 4,139,355 | 2/1979 | Turner et al. ............. 137/625.43 |
| 4,194,194 | 3/1980 | Redfern .................... 340/566 |
| 4,265,270 | 5/1981 | Satoh ...................... 251/129.12 |
| 4,294,261 | 10/1981 | Baker et al. .............. 606/202 |
| 4,340,083 | 7/1982 | Cummins .................. 137/499 |
| 4,346,728 | 8/1982 | Sulzer ..................... 137/243.6 |
| 4,492,360 | 1/1985 | Lee, II et al. ............. 251/285 |
| 4,520,819 | 6/1985 | Birmingham et al. ....... 606/202 |
| 4,556,193 | 12/1985 | Yoshiga ................... 251/248 |
| 4,593,881 | 6/1986 | Yoshino ................... 251/124 |
| 4,721,438 | 1/1988 | Ichinomiya et al. ........ 128/685 |
| 4,794,314 | 12/1988 | Janu et al. ............... 251/129.12 |
| 4,951,915 | 8/1990 | Piao ....................... 251/14 |
| 5,033,715 | 7/1991 | Chiang et al. ............. 251/129.12 |
| 5,388,984 | 2/1995 | Meslif ..................... 251/129.2 |

*Primary Examiner*—George L. Walton
*Attorney, Agent, or Firm*—Harris Beach & Wilcox

[57] ABSTRACT

A linear control valve that includes a flexible cantilevered beam having a seal mounted thereon that is arranged to open and close against a fluid port as the beam is flexed. The free end of the beam is in contact with a motor driven deflector and the amount of flexure controlled by selectively positioning the motor.

11 Claims, 3 Drawing Sheets

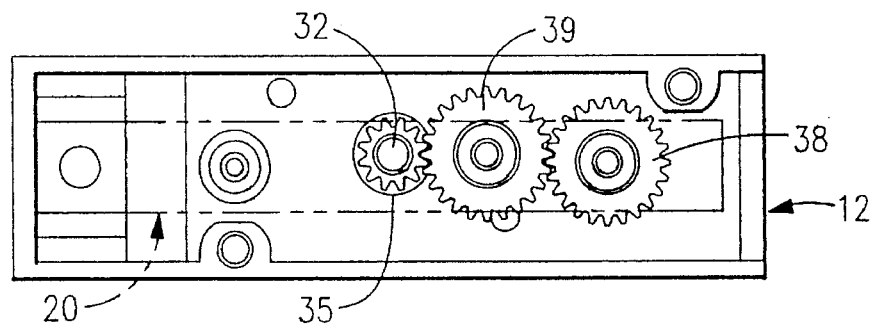
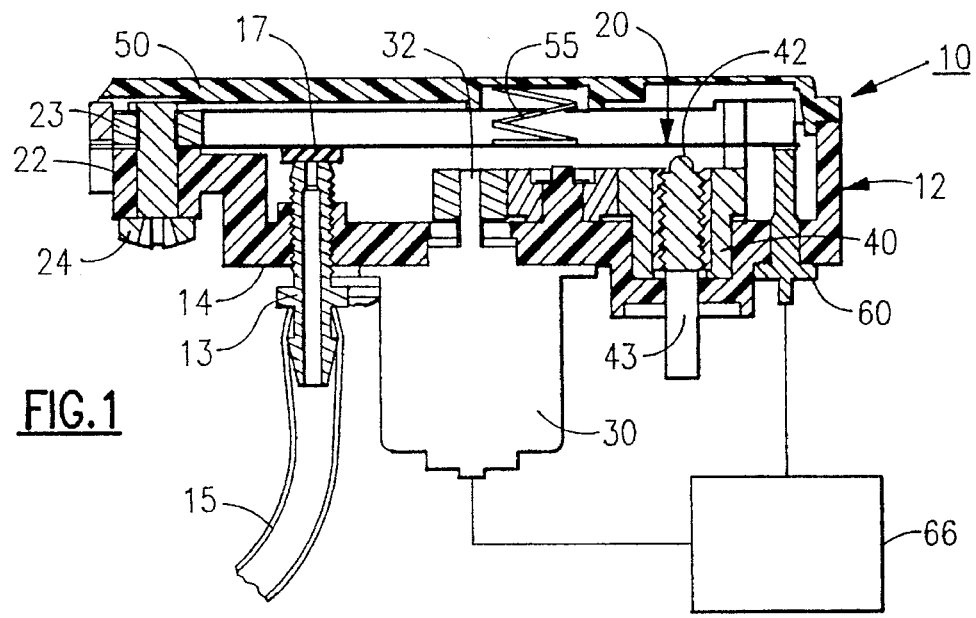
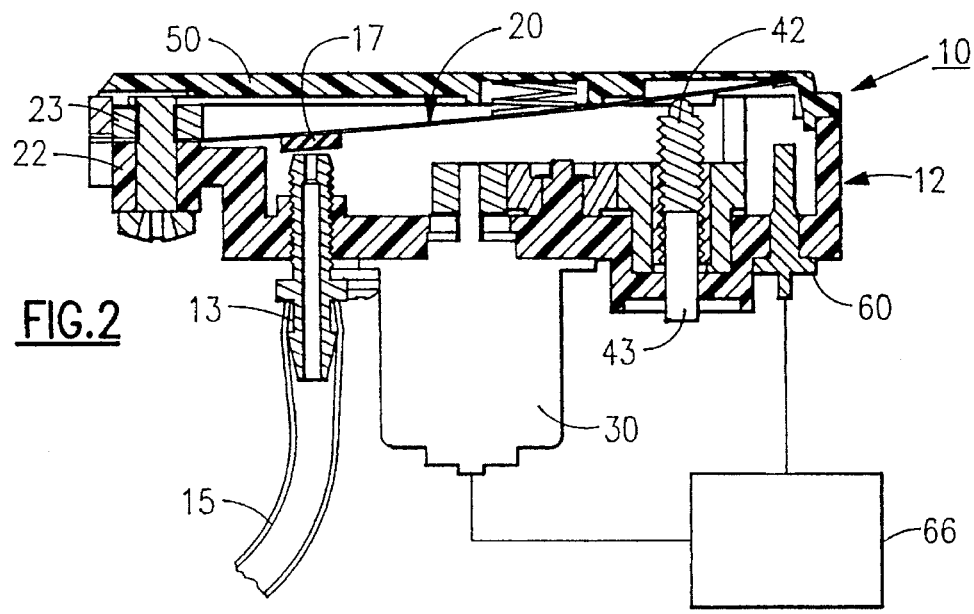

LINEAR CONTROL VALVE

BACKGROUND OF THE INVENTION

This invention relates to a control valve, and in particular, to a high resolution control valve having a linear response.

U.S. Pat. No. 4,265,270 describes a control valve in which a rigid pivotally mounted arm is tilted by a stepping motor to open or close a gas valve. The mechanism for controlling the action of the arm is very complex and draws considerable power to operate. Because of the complexity of the operating mechanism, slight movement of the stepping motor produces relatively large movement of the valve seal. Accordingly, the resolution or control that can be exercised over the valve is relatively low.

There are some linear valves that have been devised which are solenoid actuated. Here again, power consumption is relatively high.

As will be described in greater detail below, the present control valve is ideally suited for use in a blood pressure monitoring instrument and, in particular, in association with an ambulatory blood pressure monitor system. In ambulatory units, which are typically worn by the patient over an extended period of time, the control valve must be lightweight, consume low power, yet have high resolution in order to closely control the positioning of the valve as the cuff is deflated so that accurate readings can be taken.

Solenoid actuated step valves are typically used in blood pressure monitoring devices due to their small size, lower power consumption and relatively low cost. These valves provide what is called a step deflation (see FIG. 7). In the simplest systems, a large step is required because of electrical, acoustic, and pneumatic noise due to the opening and closing of the solenoid valve. This noise interferes with the detection of blood pressure pulses or Korotkof sounds used to determine blood pressure. The larger the pressure drop per step, the less accurate the system. In a system such as this, inaccuracies can be overcome by using ECG gating. This, however, requires that electrodes be placed on a patient during monitoring so that heartbeats can be synchronized during valve operation so that the system noise due to valve operation does not interfere with the detection of blood pressure pulses or Korotkof sounds. This allows much smaller step sizes and, therefore, can be more accurate. This system, while enhancing accuracy, causes patient discomfort because of electrodes and wires, and increases the costs of systems and procedures.

Because of the difficulties using step deflation, an inherently more accurate method of determining blood pressure is to deflate a cuff in a linear fashion (see FIG. 7). This is the deflation method used when taking blood pressure manually, where the technician manually controls the deflation rate through a valve. The electronic components available to provide linear deflation in a portable blood pressure monitoring device are either too expensive, too large, and/or consume too much power during operation. Through the use of the valve of the present invention, linear deflation can be accurately controlled due to the high resolution of the valve.

SUMMARY OF THE INVENTION

It is therefore a primary object of the present invention to improve automatically controlled valves and, in particular, automatically controlled valves used to deflate the cuffs of blood pressure monitors.

A further object of the present invention is to provide a low power, high resolution control valve providing a linear response for use in an ambulatory blood pressure monitor.

Another object of the present invention is to provide a low cost light weight linear control valve for use in an ambulatory blood pressure device that does not create acoustic artifacts which can interfere with readings.

These and other objects of the present invention are attained by a linear control valve that includes a flexible cantilevered beam having a seal mounted thereon that is arranged to open and close a fluid port as the beam is flexed. Movement of the beam is controlled through a motor that moves a deflector that is in contact with the free end of the beam over a predetermined path of travel. This, in turn, moves the beam between a first position wherein the fluid port is closed and a second position wherein the fluid port is fully opened.

BRIEF DESCRIPTION OF THE DRAWINGS

For a better understanding of these and other objects of the present invention, reference will be made to the following detailed description of the invention which is to be read in association with the accompanying drawings, wherein:

FIG. 1 is a side elevation of a control valve embodying the present invention showing the valve in a closed position;

FIG. 2 is also a side elevation of the present control valve showing the valve in a fully opened condition;

FIG. 3 is a top plan view of the present control valve with the top removed.

DESCRIPTION OF THE INVENTION

Figure 4:
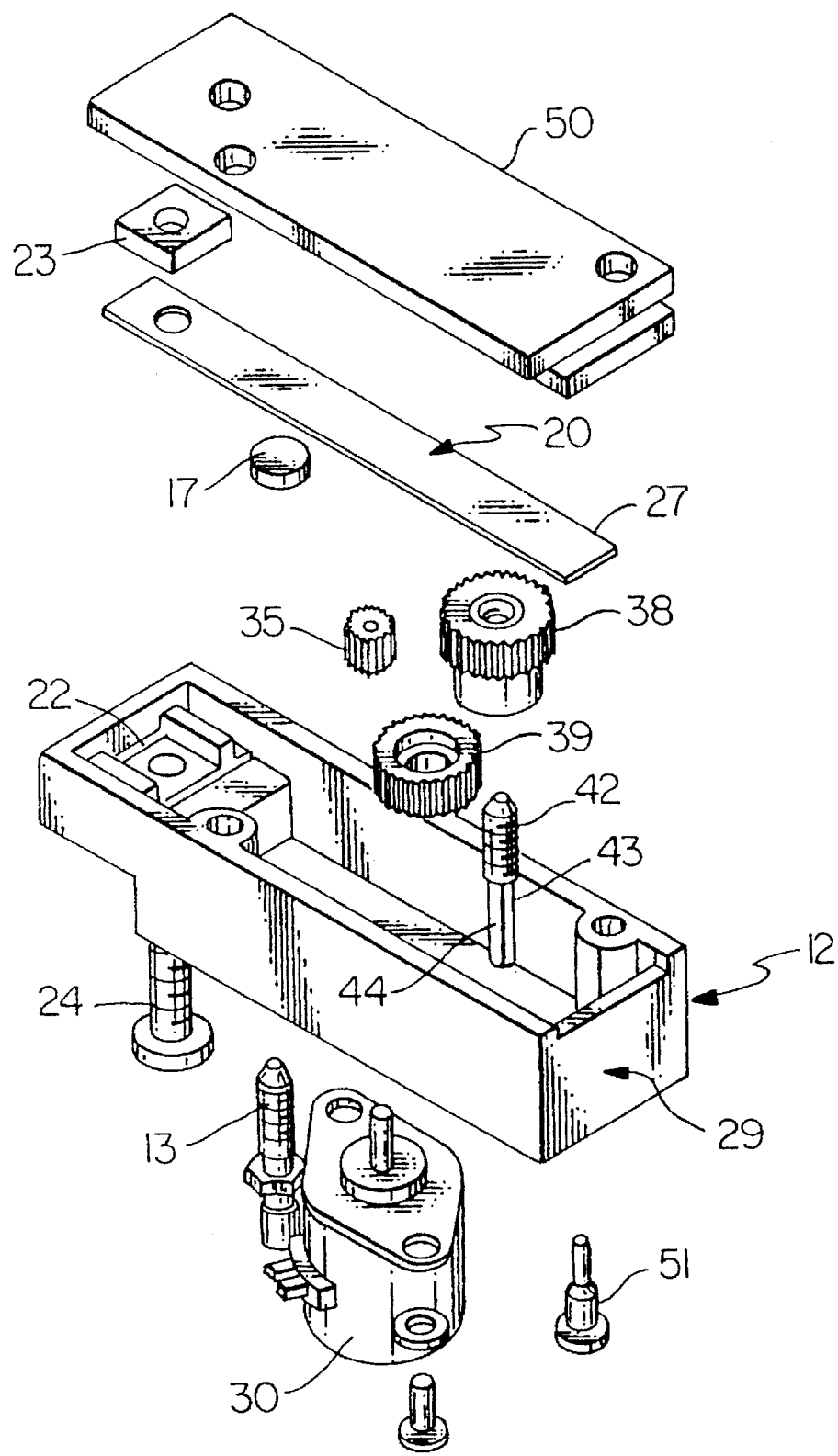
FIG. 4 is an exploded view in perspective showing in greater detail the component parts of the valve.

Referring initially to FIGS. 1–4, there is shown a control valve, generally referenced 10, that embodies the teachings of the present invention. The valve will be described with reference to an ambulatory blood pressure monitor, however, it will become evident in light of the disclosure below that the present valve has wider applications and can be used in any similar instrument requiring a linear response and high resolution. The term "resolution" as herein used, means how precisely the valve can be controlled during an opening or closing sequence. In this particular application, the valve is employed to control the deflation of an inflatable cuff of a blood pressure monitor and preferably an ambulatory blood pressure monitor.

The valve includes a light weight housing 12 that is preferably molded from a high strength plastic. An inlet port 13 is mounted in the bottom wall 14 of the housing and is connected to the cuff (not shown) of an ambulatory blood pressure monitor by means of a fluid line 15. The distal end of the inlet port contains a flat face orifice that cooperates with an elastomeric seal 17 for controlling the flow of air through the port during the cuff deflation process.

The seal is mounted on the underside of a flexible beam 20 that is mounted in cantilevered fashion inside the housing. One end of the beam is received within a contoured seat 22 that forms part of the housing. A hold down block 23 is placed over the end of the beam and a screw 24 is passed upwardly through holes provided in both the seat and the beam and is threaded into the hold down block. The screw is tightened down in assembly to pull the block down against the beam and secure the one end of the beam in the seat. The beam extends horizontally over the fluid port with the free end 27 of the beam being positioned adjacent to end wall 29 of the housing.

Sufficient room is provided within the housing to allow the beam to flex from a first position shown in FIG. 1 and a second fully flexed position as shown in FIG. 2. When the beam is in the first position, the seal 17 is closed against the fluid port, thus preventing fluid from passing through the port. When the beam is in the fully flexed position, the seal is removed from the port which, at this time, is in a fully or wide opened condition. In an alternative embodiment, the seal 17 may comprise all or part of the fluid port. As will be explained below, the position of the beam can be accurately controlled as it moves between the two extreme positions to provide the valve with high resolution and a linear response. The beam is formed preferably of beryllium copper or any other suitable spring material.

A stepping motor 30 is secured to the bottom wall of the housing using threaded fasteners such as screws 31 (FIG. 4). The drive shaft 32 of the motor passes upwardly through an opening in the bottom wall into the housing. A drive pinion 35 (FIG.3) is secured to the shaft for rotation therewith. The drive pinion is coupled to a driven gear 38 through an intermediate gear 39. The hub 40 of the driven gear 38 is seated in a circular opening formed in the bottom wall of the housing. A threaded lead screw 42 is mated by female threads formed in an axial opening passing through the drive gear. The lead screw is provided with a shank 43 that passes out of the bottom of the driven gear and is received in a hole formed in the bottom wall of the housing. A flat surface 44 is machined along the shank which mates with a complementary flat surface formed along the shank receiving opening so that the lead screw is prevented from rotating in assembly.

As can be seen, as the stepping motor turns in one direction, the driven gear is turned in the same direction to advance the lead screw upwardly into contact with the free end of the beam. Continued turning of the motor causes the tip of the lead screw to flex the beam, thus lifting the seal from the fluid port allowing fluid to pass through the port. The present motor is designed to operate at 5 volts and turn about 18° per step.

The seal is located a predetermined distance from the point where the lead screw contacts the free end of the beam. The seal is displaced a distance that is a fraction of the lead screw travel during each motor actuation. This, coupled with the reduction gear drive arrangement, provides for enhanced resolution and close control over the flow of air moving through the port during cuff deflation, since it is the distance between the seal and the port which determines the flow rate.

The housing is closed by means of a top cover 50 that is held in place by threaded fasteners such as screw 5 (FIG.4) that is passed upwardly through holes 52 and threaded into the cover. An optional biasing spring 55 is mounted in the cover which applies pressure against the top of the beam urging the beam downwardly into the first port closing position.

A sensing pin contact 61 is mounted in the floor of the housing and extends upwardly as shown in FIG. 1 so that the distal tip of the pin closes against the free end of the beam when the beam is in the first port closing position. An electrical circuit (not shown) is closed causing a signal to be sent to controller 66 indicating that the valve port is closed. The controller is also connected to the stepping motor and is programmed through suitable software to regulate the operation of the motor and thus, the deflation of the cuff.

Figure 7:
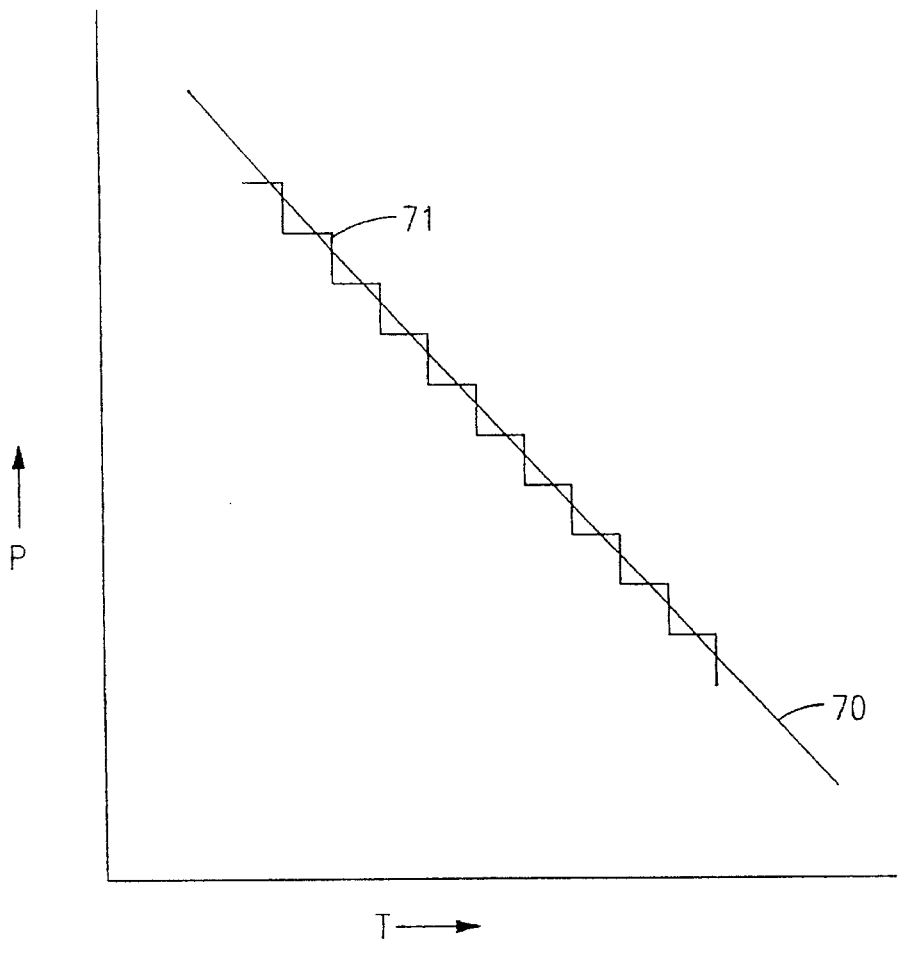
FIG. 7 is a graphic representation comparing the response of the present control valve with that of a solenoid actuated control valve.

FIG. 7 graphically illustrates the function of the current control valve in comparison with a typical solenoid operated control valve as a blood pressure cuff is being deflated. The graph compares pressure (P) against the time (T). The linear response is depicted by the straight line response curve 70, while that of the solenoid valve is depicted by the stepped response curve 71. Clearly, the solenoid valves cannot deliver the same high resolution performance of the present valve.

Figure 5:
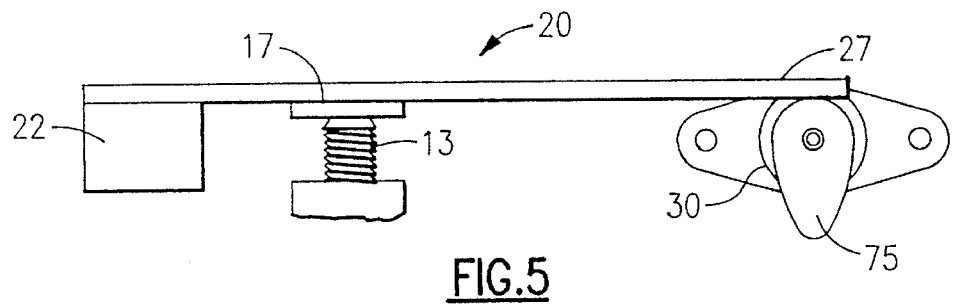
FIG. 5 is a schematic side elevation showing a further embodiment of the invention.

FIG. 5 illustrates a further embodiment of the invention in which a cam 75 is connected directly to the drive shaft of stepping motor 30. The cam is profiled to impart a desired motion to the free end of the beam to provide the desired linear, high resolution response needed to control cuffs.

Figure 6:
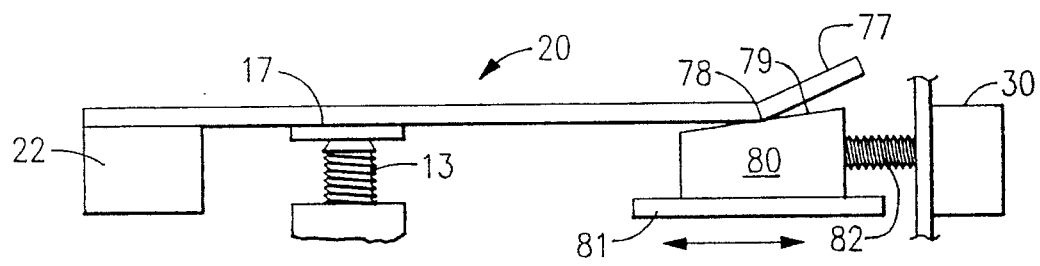
FIG. 6 is another schematic side elevation showing still another embodiment of the invention.

A still further embodiment of the invention is illustrated in FIG. 6. In this case, the distal end 77 of the beam is turned upwardly to provide a curved contact surface 78 that is adapted to ride in contact against the inclined surface 79 of wedge 80. The wedge is arranged to ride within a guideway 81 beneath the beam. The wedge is driven along a reciprocal path of travel along the guideway by means of stepper motor 30. The drive shaft 82 of the motor is threaded. The male thread on the shaft are mated with female threads formed in the wedge body so that the-wedge is advanced or retracted as the motor turns to again flex the beam.

It should be understood that in certain applications, a stepper motor would not be necessary with the valve of the present invention.

While this invention has been explained with reference to the structure disclosed herein, it is not confined to the details set forth and this invention is intended to cover any modifications and changes as may come within the scope of the following claims:

What is claimed is:

1. A linear control valve suitable for providing fluid control which includes valve housing,
    a flexible cantilevered beam located within said housing, said beam having one end that is secured against movement, and a free end,
    said beam being made of a spring material and arranged to close against the seal means of a fluid port positioned adjacent said secured end when said beam is in a first position, and to fully open said port when said beam is flexed to a second position,
    deflecting means acting on said free end of said beam for flexing the beam about said secured end between said first and second positions, and
    a motor secured to said housing and connected to said deflecting means for selectively positioning said deflecting means into and out of engagement with said free end to flex and move said beam between said first and second positions thereby controlling fluid flow through said port.

2. The control valve of claim 1 that further includes a control means connected to the drive means for controlling the positioning of said beam between said first and second positions.

3. The control valve of claim 1 that further includes a speed reduction means acting between the motor and said deflecting means for increasing the resolution of the valve.

4. The control valve of claim 1 wherein said deflecting means is a lead screw.

5. The control valve of claim 1 wherein said deflecting means is a cam.

6. The control means of claim 1 wherein said deflecting means is a sliding wedge.

7. The control means of claim 1 that further includes a sensor means for detecting the open or closed position of said valve.

8. A linear control valve for deflating the cuff of a blood pressure monitor that includes a housing having a fluid entrance port connected to the inflatable cuff of a blood pressure monitor, a flexible beam secured at one end in said housing and the other end being free to move, said beam passing over said port, a seal mounted upon said beam adjacent said secured end, said seal being arranged to close against said port when said beam is in a first position and to fully open said port when said beam is flexed to a second position thereby deflating said cuff, a lead screw mounted for rotation in said housing and being arranged to contact the free end of said beam and position said beam between said first and second position as said lead screw is advanced and retracted within said housing, a motor secured to said housing and connected to said lead screw to incrementally advance and retract said lead screw into and out of engagement with said free end and thereby position the beam between said first and second positions.

9. The control valve of claim 8 that further includes reduction gears mounted between the motor and said lead screw for increasing the resolution of said valve.

10. The control valve of claim 8 that further includes a sensor means for detecting the open or closed position of said valve.

11. The control valve of claim 8 wherein said seal is formed of an elastomeric material.

* * * * *